(12) United States Patent
Hiltke et al.

(10) Patent No.: US 7,429,388 B2
(45) Date of Patent: Sep. 30, 2008

(54) **VACCINE FOR NONTYPEABLE *HAEMOPHILUS INFLUENZAE* INFECTION**

(75) Inventors: Thomas Hiltke, New Market, MD (US); Timothy F. Murphy, East Amherst, NY (US); Sanjay Sethi, East Amherst, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 324 days.

(21) Appl. No.: 11/096,850

(22) Filed: Apr. 1, 2005

(65) Prior Publication Data

US 2005/0266030 A1    Dec. 1, 2005

Related U.S. Application Data

(60) Provisional application No. 60/558,639, filed on Apr. 1, 2004.

(51) Int. Cl.
*A61K 39/02* (2006.01)
*A61K 39/116* (2006.01)
*A61K 39/00* (2006.01)
*A61K 38/00* (2006.01)
*C07K 1/00* (2006.01)

(52) U.S. Cl. .............. 424/256.1; 424/234.1; 424/203.1; 424/190.1; 424/184.1; 514/2; 530/350; 530/824

(58) Field of Classification Search .............. 424/190.1, 424/234.1, 256.1, 203.1, 184.1; 514/2; 530/350, 530/825
See application file for complete search history.

(56) References Cited

U.S. PATENT DOCUMENTS 6,673,538 B1   1/2004   Goldstein

*Primary Examiner*—S. Devi
(74) *Attorney, Agent, or Firm*—Hodgson Russ LLP (57) ABSTRACT

This invention provides a method for identifying strains of nontypeable *Haemophilus influenzae* that can be used as immunogenic compositions having specificity against a plurality of *Haemophilus influenzae* strains. The invention also provides compositions comprising whole cell bacteria or outer membrane protein P2 obtained from the strains for use as vaccines.

9 Claims, 5 Drawing Sheets

```
┌─────────────────────────────────────┐
│ Obtain OMP P2 amino acid sequences from │──10
│     a plurality of NTHI strains     │
└─────────────────────────────────────┘
                 ↓
┌─────────────────────────────────────┐
│   Align and compare P2 the amino acid │──20
│              sequences              │
└─────────────────────────────────────┘
                 ↓
┌─────────────────────────────────────┐
│  Construct a relatedness tree based on the │──30
│          sequence comparison        │
└─────────────────────────────────────┘
                 ↓
┌─────────────────────────────────────┐
│  Group the strains based on relatedness of │──40
│              P2 sequences           │
└─────────────────────────────────────┘
                 ↓
┌─────────────────────────────────────┐
│  Select one or more Representative strains │
│    from the groups based on greatest degrees │──50
│     of P2 sequence relatedness to other │
│          members of the group       │
└─────────────────────────────────────┘
                 ↓
┌─────────────────────────────────────┐
│     Optionally testing the selected │──60
│  Representative strains for cross-reactivity │
│          with other NTHI strains    │
└─────────────────────────────────────┘
                 ↓
┌─────────────────────────────────────┐
│     Identify strains for preparation of │
│    immunogenic compositions based on │──70
│   greatest degrees of relatedness to other │
│   members of the group or cross-reactivity to │
│           other NTHI strains        │
└─────────────────────────────────────┘
```

Figure 1.

Amino acid sequence of NTHI strain 13P24H1 OMP P2 protein (SEQ ID NO:1):

AVVYNNEGTNVELGGRLSIIAEQSNSTIKDQKQQHGALRNQGSRFHIKATHNFGDGF
YAQGYLETRLVSAQSGTESDNFGHIITKYAYVTLGNKALGEVKLGRAKTIADGITSA
EDKEYGVLNNSKYIPTDGNTVGYTFKGIDGLVLGANYLLAQERHKYTGAGAGAVA
GEVYQQKISNGVQVGAKYDANNIIAGIAYGRTNYREDIIAGSDSGKKQQVNGALSTL
GYRFSDLGLLVSLDSGYAKTKNYKAKHEKSYFVSPGFQYELMEDTNFYGNFKYERN
SVDQGKKEREHAVLFGVDHKLHKQVLTYIEGAYARTRTTQATGTKVKTEKEKSVG
VGLRVYF

Amino acid sequence of NTHI strain 23P2H1 OMP P2 protein (SEQ ID NO:2):

AVVYNNEGTKVELGGRLSVIAEQSSNTLDDQKQQHGALRNQGSRFHIKATHNFGDG
FYAQGYLETRLVTNPNGFTHEDRDGFGDITTKYAYVTLGNKALGEVKLGRAKTIAD
GITSAEDKEYGVLNNSKYVPTNGNTAGYTFKGIDGLVLGANYLLAQKYDNAGAND
GEVQKQSISNGVQVGAKYDANNIVAAIAFGRTNYKEDNSPCASKRKEQLKGVLSTL
GYRFSDLGLLVSLDSGYAKTKNHKKHIPAAAAAAAAAAYDEKRYFVSPGFQYELME
DTNVYGNFKYERNSSDQGKKTHEQAVLFGVDHKLHKQVLTYIEGAYARTKTNEKG
QTEKTEKEKSVGVGLRVYF

Amino acid sequence of NTHI strain 54P24H1 OMP P2 protein (SEQ ID NO:3):

AVVYNNEGTNVELGGRLSVIAEQSNSTADDQKQQHGALRNQGSRFHIKATHNFGDG
FYAQGYLETRFVTKASENGSDNFGDITTKYAYVTLGNKAFGEVKLGRAKTIADGITS
AEDKEYGVIKNSKYIPTNGNTIGYTFKGIDGLVLGANYLLAQERYEGEVNPQKISNG
VQVGAKYDANNIIAGIAYGRTNYRENTIGIPDLGKKQQVNGALSTLGYRFSDLGLLV
SLDSGYAKTKNYKAKHEKRYFVSPGFQYELMEDTNVYGNFKYERNSVDQGKKTRE
HAVLFGVDHKLHKQLLTYIEGAYARTRTTSGTNVTTEKEKSVGVGLRVYF

Amino acid sequence of NTHI strain 47P12H1 OMP P2 protein (SEQ ID NO:4):

AVVYNNEGTNVELGGRLSVIAEQSNSTADDQKQQHGALRNQGSRFHIKATHNFGDG
FYAQGYLETRFVTKASENGSDNFGDITTKYAYVTLGNKAFGEVKLGRAKTIADGITS
AEDKEYGVIKNSKYIPTNGNTIGYTFKGIDGLVLGANYLLAQERYEGEVNPQKISNG
VQVGAKYDANNIIAGIAYGRTNYRENTIGIPGLGKKQQVNGALSTLGYRFSDLGLLV
SLDSGYAKTKNYKAKHEKRYFLSPGFQYELMEDTNVYGNFKYERNSVDQGKKTRE
HAVLFGVDHKLHKQLLTYIEGAYARTRTTSGTNVTTEKEKSVGVGLRVYF

Amino acid sequence of NTHI strain 31P7H7 OMP P2 protein (SEQ ID NO:5):

AVVYNNEGTNVELDGHLSVIAEQSSNTLDDQKQQHGALRNQGSRFHIKATHNFGDG
FYAQGYLETRFVSKYKDNADHFDSITTKYAYVTLGNKALGEVKLGRAKTIADGITSA
EDKEYGVLNNSKYIPTNGNTVGYTFEGIDGLVLGANYLLAQQRNAHSGAAGEVVAQ
AISNGVQVGAKYDANNIIAGIAYGRTNYREDLAIQDKSGKKQQVNGALSTLGYRFSD
LGLLVSLDSGYAKTKNYKDKHEKRYFVSPGFQYELMEDTNVYGNFKYERNSVDQG
KKAREHAVLFGVDHKLHKQVLTYIEGAYARTRTNDKGKTEKTEKEKSVGVGLRVY
F

| | 2.5% Serum | | | |
|---|---|---|---|---|
| Target Strain | 13P24H1 | 23P2H1 | 54P24H1 | PBS |
| 5P30H1 | + | + | NK | NK |
| 31P7H7 | +++ | +++ | +++ | NK |
| 73P2H1 | NK | NK | +++ | + |
| 14P1H1 | NK | ++ | +++ | NK |
| 14P14H1 | +++ | +++ | ++ | NK |
| 22P1H1 | +++ | NK | NK | NK |
| 47P12H1 | NK | NK | NK | NK |
| 48P29H1 | NK | NK | NK | NK |
| 6P5H1 | NK | NK | NK | NK |
| 74P1H. | +++ | NK | + | NK |
| 5P19H1 | +++ | NK | NK | NK |
| 24P17H1 | +++ | NK | + | NK |
| 32P8H2 | NK | NK | NK | NK |
| (otitis media strains) | | | | NK |
| 3723 | NK | NK | NK | NK |
| 1174 | + | NK | NK | NK |
| 1749 | NK | +++ | NK | NK |
| 438 | NK | NK | | NK |
| C1337 | NK | NK | +++ | NK |
| C1359 | NK | NK | +++ | NK |
| C1484 | NK | + | + | NK |
| DL200 | NK | +++ | NK | NK |
| 1826 | NK | NK | NK | NK |
| 7173 | NK | ++ | NK | NK |
| 6699 | ++ | NK | NK | NK |
| 6700 | +++ | NK | NK | NK |
| C1476 | NK | NK | NK | NK |

2.5% serum (Immunization strain)

| Strain | Source | 13P24 | 23P2 | 54P24 | 47P12 | 32P8 | 6P5 | 31P7 |
|---|---|---|---|---|---|---|---|---|
| 23P2H1 | COPD (Buffalo, NY) | ND | +++ | ND | NK | NK | NK | ND |
| 13P24H1 | COPD (Buffalo, NY) | +++ | NK | + | NK | NK | NK | + |
| 54P24H1 | COPD (Buffalo, NY) | +++ | +++ | +++ | + | NK | + | + |
| 47P12H1 | COPD (Buffalo, NY) | NK | NK | NK | +++ | NK | NK | NK |
| 32P8H2 | COPD (Buffalo, NY) | NK | NK | NK | NK | NK | NK | NK |
| 6P5H1 | COPD (Buffalo, NY) | +++ | +++ | ++ | NK | NK | +++ | +++ |
| 74P11H1 | COPD (Buffalo, NY) | ++ | ++ | NK | NK | NK (?) | ++ | ND |
| 5P30h1 | COPD (Buffalo, NY) | NK | +++ | NK | NK | + | NK | NK |
| 31P7H7 | COPD (Buffalo, NY) | +++ | +++ | +++ | + | +++ | + | +++ |
| 73P2H1 | COPD (Buffalo, NY) | NK | NK | ++ | NK | NK | NK | ND |
| 14P1H1 | COPD (Buffalo, NY) | ++ | ++ | + | NK | NK | NK | ND |
| 14P14H1 | COPD (Buffalo, NY) | +++ | +++ | +++ | NK | +++ | +++ | ND |
| 22P1H1 | COPD (Buffalo, NY) | NK | NK | NK | NK | NK | NK | ND |
| 48P29H1 | COPD (Buffalo, NY) | ++ | ++ | ++ | NK | NK | NK | NK |
| 74P1H1 | COPD (Buffalo, NY) | +++ | NK | + | NK | NK | NK | NK |
| 5P19H1 | COPD (Buffalo, NY) | + | + | + | + | + | + | + |
| 24P17H1 | COPD (Buffalo, NY) | +++ | +++ | NK | NK | NK | +++ | +++ |
| 3723 | MEF (Buffalo, NY) | NK | NK | NK | NK | NK | NK | NK |
| 1174 | MEF (Buffalo, NY) | + | ++ | NK | NK | NK | NK | NK |
| 1749 | MEF (Buffalo, NY) | NK | NK | NK | NK | NK | NK | NK |
| 438 | MEF (Buffalo, NY) | NK | NK | NK | NK | NK | NK | NK |
| C1337 | MEF (Seattle, WA) | NK | NK | NK | NK | NK | NK | NK |
| C1359 | MEF (Seattle, WA) | NK | NK | NK | NK | NK | NK | NK |
| C1484 | MEF (Seattle, WA) | + | NK | + | NK | NK | NK | NK |
| DL200 | MEF (Dallas, TX) | ++ | ++ | ++ | ++ | ++ | ++ | +++ |
| 1826 | MEF (Buffalo, NY) | NK | NK | NK | NK | NK | NK | NK |
| 7173 | MEF (Buffalo, NY) | NK | + | NK | NK | NK | NK | NK |
| 6699 | MEF (Buffalo, NY) | ++ | NK | NK | NK | NK | NK | NK |
| 6700 | MEF (Buffalo, NY) | +++ | +++ | NK | NK | NK | NK | +++ |
| C1467 | MEF (Seattle, WA) | NK | NK | NK | NK | NK | NK | NK |
| 7P49H1 | COPD (Buffalo, NY) | NK | NK | NK | +++ | NK | NK | NK |
| C1425 | MEF (Seattle, WA) | NK | NK | NK | NK | NK | NK | ND |
| 2536 | MEF (Buffalo, NY) | NK | NK | NK | (NK)* | NK | NK | ND |
| 11P6H1 | COPD (Buffalo, NY) | NK | ++ | NK | NK | NK | + | NK |
| 67P13H1 | COPD (Buffalo, NY) | +++ | +++ | NK | +++ | +++ | +++ | ++ |
| 18P17H1 | COPD (Buffalo, NY) | ++ | +++ | +++ | NK | ++ | NK | NK |
| % strains killed | | 41.67% | 38.89% | 38.89% | 13.89% | 19.44% | 25.00% | 25.0%* |

Total % strains killed = 86.1%

Key
NK = no kill
"+" = 50-69.9% kill
"++" = 70-89.9% kill
"+++" = 90-100% kill
ND = not done 50-100% Kill MEF = middle ear effusion
* = incomplete data

SEQUENCE LISTING

```
<160> NUMBER OF SEQ ID NOS: 5

<210> SEQ ID NO 1
<211> LENGTH: 344
<212> TYPE: PRT
<213> ORGANISM: NTHI strain 13P24H1 OMP P2 protein
<220> FEATURE:

<400> SEQUENCE: 1

Ala Val Val Tyr Asn Asn Glu Gly Thr Asn Val Glu Leu Gly Gly
                5                   10                  15

Arg Leu Ser Ile Ile Ala Glu Gln Ser Asn Ser Thr Ile Lys Asp
                20                  25                  30

Gln Lys Gln Gln His Gly Ala Leu Arg Asn Gln Gly Ser Arg Phe
                35                  40                  45

His Ile Lys Ala Thr His Asn Phe Gly Asp Gly Phe Tyr Ala Gln
                50                  55                  60

Gly Tyr Leu Glu Thr Arg Leu Val Ser Ala Gln Ser Gly Thr Glu
                65                  70                  75

Ser Asp Asn Phe Gly His Ile Ile Thr Lys Tyr Ala Tyr Val Thr
                80                  85                  90

Leu Gly Asn Lys Ala Leu Gly Glu Val Lys Leu Gly Arg Ala Lys
                95                  100                 105

Thr Ile Ala Asp Gly Ile Thr Ser Ala Glu Asp Lys Glu Tyr Gly
                110                 115                 120

Val Leu Asn Asn Ser Lys Tyr Ile Pro Thr Asp Gly Asn Thr Val
                125                 130                 135

Gly Tyr Thr Phe Lys Gly Ile Asp Gly Leu Val Leu Gly Ala Asn
                140                 145                 150

Tyr Leu Leu Ala Gln Glu Arg His Lys Tyr Thr Gly Ala Gly Ala
                155                 160                 165

Gly Ala Val Ala Gly Glu Val Tyr Gln Gln Lys Ile Ser Asn Gly
                170                 175                 180

Val Gln Val Gly Ala Lys Tyr Asp Ala Asn Asn Ile Ile Ala Gly
                185                 190                 195

Ile Ala Tyr Gly Arg Thr Asn Tyr Arg Glu Asp Ile Ile Ala Gly
                200                 205                 210

Ser Asp Ser Gly Lys Lys Gln Gln Val Asn Gly Ala Leu Ser Thr
                215                 220                 225

Leu Gly Tyr Arg Phe Ser Asp Leu Gly Leu Leu Val Ser Leu Asp
                230                 235                 240

Ser Gly Tyr Ala Lys Thr Lys Asn Tyr Lys Ala Lys His Glu Lys
                245                 250                 255

Ser Tyr Phe Val Ser Pro Gly Phe Gln Tyr Glu Leu Met Glu Asp
                260                 265                 270

Thr Asn Phe Tyr Gly Asn Phe Lys Tyr Glu Arg Asn Ser Val Asp
                275                 280                 285
```

```
Gln Gly Lys Lys Glu Arg Glu His Ala Val Leu Phe Gly Val Asp
            290                 295                 300

His Lys Leu His Lys Gln Val Leu Thr Tyr Ile Gly Ala Tyr
            305                 310                 315

Ala Arg Thr Arg Thr Thr Gln Ala Thr Gly Thr Lys Val Lys Thr
            320                 325                 330

Glu Lys Glu Lys Ser Val Gly Val Gly Leu Arg Val Tyr Phe
            335                 340                 344

<210> SEQ ID NO 2
<211> LENGTH: 353
<212> TYPE: PRT
<213> ORGANISM: NTHI strain 23P2H1 OMP P2 protein
<220> FEATURE:

<400> SEQUENCE: 2

Ala Val Val Tyr Asn Asn Glu Gly Thr Lys Val Glu Leu Gly Gly
              5                  10                  15

Arg Leu Ser Val Ile Ala Glu Gln Ser Asn Thr Leu Asp Asp
             20                  25                  30

Gln Lys Gln Gln His Gly Ala Leu Arg Asn Gln Gly Ser Arg Phe
             35                  40                  45

His Ile Lys Ala Thr His Asn Phe Gly Asp Gly Phe Tyr Ala Gln
             50                  55                  60

Gly Tyr Leu Glu Thr Arg Leu Val Thr Asn Pro Asn Gly Phe Thr
             65                  70                  75

His Glu Asp Arg Asp Gly Phe Gly Asp Ile Thr Thr Lys Tyr Ala
             80                  85                  90

Tyr Val Thr Leu Gly Asn Lys Ala Leu Gly Glu Val Lys Leu Gly
             95                 100                 105

Arg Ala Lys Thr Ile Ala Asp Gly Ile Thr Ser Ala Glu Asp Lys
            110                 115                 120

Glu Tyr Gly Val Leu Asn Asn Ser Lys Tyr Val Pro Thr Asn Gly
            125                 130                 135

Asn Thr Ala Gly Tyr Thr Phe Lys Gly Ile Asp Gly Leu Val Leu
            140                 145                 150

Gly Ala Asn Tyr Leu Leu Ala Gln Lys Tyr Asp Asn Ala Gly Ala
            155                 160                 165

Asn Asp Gly Glu Val Gln Lys Gln Ser Ile Ser Asn Gly Val Gln
            170                 175                 180

Val Gly Ala Lys Tyr Asp Ala Asn Asn Ile Val Ala Ala Ile Ala
            185                 190                 195

Phe Gly Arg Thr Asn Tyr Lys Glu Asp Asn Ser Pro Cys Ala Ser
            200                 205                 210

Lys Arg Lys Glu Gln Leu Lys Gly Val Leu Ser Thr Leu Gly Tyr
            215                 220                 225

Arg Phe Ser Asp Leu Gly Leu Leu Val Ser Leu Asp Ser Gly Tyr
            230                 235                 240

Ala Lys Thr Lys Asn His Lys Lys His Ile Pro Ala Ala Ala Ala
            245                 250                 255

Ala Ala Ala Ala Ala Ala Tyr Asp Glu Lys Arg Tyr Phe Val Ser
            260                 265                 270

Pro Gly Phe Gln Tyr Glu Leu Met Glu Asp Thr Asn Val Tyr Gly
            275                 280                 285
```

```
Asn Phe Lys Tyr Glu Arg Asn Ser Ser Asp Gln Gly Lys Lys Thr
                290                 295                 300

His Glu Gln Ala Val Leu Phe Gly Val Asp His Lys Leu His Lys
                305                 310                 315

Gln Val Leu Thr Tyr Ile Glu Gly Ala Tyr Ala Arg Thr Lys Thr
                320                 325                 330

Asn Glu Lys Gly Gln Thr Glu Lys Thr Glu Lys Glu Lys Ser Val
                335                 340                 345

Gly Val Gly Leu Arg Val Tyr Phe
                350         353

<210> SEQ ID NO 3
<211> LENGTH: 332
<212> TYPE: PRT
<213> ORGANISM: NTHI strain 54P24H1 OMP P2 protein
<220> FEATURE:

<400> SEQUENCE: 3

Ala Val Val Tyr Asn Asn Glu Gly Thr Asn Val Glu Leu Gly Gly
                  5                  10                  15

Arg Leu Ser Val Ile Ala Glu Gln Ser Asn Ser Thr Ala Asp Asp
                 20                  25                  30

Gln Lys Gln Gln His Gly Ala Leu Arg Asn Gln Gly Ser Arg Phe
                 35                  40                  45

His Ile Lys Ala Thr His Asn Phe Gly Asp Gly Phe Tyr Ala Gln
                 50                  55                  60

Gly Tyr Leu Glu Thr Arg Phe Val Thr Lys Ala Ser Glu Asn Gly
                 65                  70                  75

Ser Asp Asn Phe Gly Asp Ile Thr Thr Lys Tyr Ala Tyr Val Thr
                 80                  85                  90

Leu Gly Asn Lys Ala Phe Gly Glu Val Lys Leu Gly Arg Ala Lys
                 95                 100                 105

Thr Ile Ala Asp Gly Ile Thr Ser Ala Glu Asp Lys Glu Tyr Gly
                110                 115                 120

Val Ile Lys Asn Ser Lys Tyr Ile Pro Thr Asn Gly Asn Thr Ile
                125                 130                 135

Gly Tyr Thr Phe Lys Gly Ile Asp Gly Leu Val Leu Gly Ala Asn
                140                 145                 150

Tyr Leu Leu Ala Gln Glu Arg Tyr Glu Gly Glu Val Asn Pro Gln
                155                 160                 165

Lys Ile Ser Asn Gly Val Gln Val Gly Ala Lys Tyr Asp Ala Asn
                170                 175                 180

Asn Ile Ile Ala Gly Ile Ala Tyr Gly Arg Thr Asn Tyr Arg Glu
                185                 190                 195

Asn Thr Ile Gly Ile Pro Asp Leu Gly Lys Lys Gln Gln Val Asn
                200                 205                 210

Gly Ala Leu Ser Thr Leu Gly Tyr Arg Phe Ser Asp Leu Gly Leu
                215                 220                 225

Leu Val Ser Leu Asp Ser Gly Tyr Ala Lys Thr Lys Asn Tyr Lys
                230                 235                 240

Ala Lys His Glu Lys Arg Tyr Phe Val Ser Pro Gly Phe Gln Tyr
                245                 250                 255

Glu Leu Met Glu Asp Thr Asn Val Tyr Gly Asn Phe Lys Tyr Glu
                260                 265                 270

Arg Asn Ser Val Asp Gln Gly Lys Lys Thr Arg Glu His Ala Val
```

```
                275                 280                 285
Leu Phe Gly Val Asp His Lys Leu His Lys Gln Leu Leu Thr Tyr
            290                 295                 300
Ile Glu Gly Ala Tyr Ala Arg Thr Arg Thr Thr Ser Gly Thr Asn
            305                 310                 315
Val Thr Thr Glu Lys Glu Lys Ser Val Gly Val Gly Leu Arg Val
            320                 325                 330
Tyr Phe
    332

<210> SEQ ID NO 4
<211> LENGTH: 332
<212> TYPE: PRT
<213> ORGANISM: NTHI strain 47P12H1 OMP P2 protein
<220> FEATURE:

<400> SEQUENCE: 4

Ala Val Val Tyr Asn Asn Glu Gly Thr Asn Val Glu Leu Gly Gly
              5                  10                  15
Arg Leu Ser Val Ile Ala Glu Gln Ser Asn Ser Thr Ala Asp Asp
             20                  25                  30
Gln Lys Gln Gln His Gly Ala Leu Arg Asn Gln Gly Ser Arg Phe
             35                  40                  45
His Ile Lys Ala Thr His Asn Phe Gly Asp Gly Phe Tyr Ala Gln
             50                  55                  60
Gly Tyr Leu Glu Thr Arg Phe Val Thr Lys Ala Ser Glu Asn Gly
             65                  70                  75
Ser Asp Asn Phe Gly Asp Ile Thr Thr Lys Tyr Ala Tyr Val Thr
             80                  85                  90
Leu Gly Asn Lys Ala Phe Gly Glu Val Lys Leu Gly Arg Ala Lys
             95                 100                 105
Thr Ile Ala Asp Gly Ile Thr Ser Ala Glu Asp Lys Glu Tyr Gly
            110                 115                 120
Val Ile Lys Asn Ser Lys Tyr Ile Pro Thr Asn Gly Asn Thr Ile
            125                 130                 135
Gly Tyr Thr Phe Lys Gly Ile Asp Gly Leu Val Leu Gly Ala Asn
            140                 145                 150
Tyr Leu Leu Ala Gln Glu Arg Tyr Glu Gly Glu Val Asn Pro Gln
            155                 160                 165
Lys Ile Ser Asn Gly Val Gln Val Gly Ala Lys Tyr Asp Ala Asn
            170                 175                 180
Asn Ile Ile Ala Gly Ile Ala Tyr Gly Arg Thr Asn Tyr Arg Glu
            185                 190                 195
Asn Thr Ile Gly Ile Pro Gly Leu Gly Lys Lys Gln Gln Val Asn
            200                 205                 210
Gly Ala Leu Ser Thr Leu Gly Tyr Arg Phe Ser Asp Leu Gly Leu
            215                 220                 225
Leu Val Ser Leu Asp Ser Gly Tyr Ala Lys Thr Lys Asn Tyr Lys
            230                 235                 240
Ala Lys His Glu Lys Arg Tyr Phe Leu Ser Pro Gly Phe Gln Tyr
            245                 250                 255
Glu Leu Met Glu Asp Thr Asn Val Tyr Gly Asn Phe Lys Tyr Glu
            260                 265                 270
Arg Asn Ser Val Asp Gln Gly Lys Lys Thr Arg Glu His Ala Val
            275                 280                 285
```

```
Leu Phe Gly Val Asp His Lys Leu His Lys Gln Leu Leu Thr Tyr
                290                 295                 300

Ile Glu Gly Ala Tyr Ala Arg Thr Arg Thr Thr Ser Gly Thr Asn
                305                 310                 315

Val Thr Thr Glu Lys Glu Lys Ser Val Gly Val Gly Leu Arg Val
                320                 325                 330

Tyr Phe
    332

<210> SEQ ID NO 5
<211> LENGTH: 337
<212> TYPE: PRT
<213> ORGANISM: NTHI strain 31P7H7 OMP P2 protein
<220> FEATURE:

<400> SEQUENCE: 5

Ala Val Val Tyr Asn Asn Glu Gly Thr Asn Val Glu Leu Asp Gly
                  5                  10                  15

His Leu Ser Val Ile Ala Glu Gln Ser Asn Thr Leu Asp Asp
                 20                  25                  30

Gln Lys Gln Gln His Gly Ala Leu Arg Asn Gln Gly Ser Arg Phe
                 35                  40                  45

His Ile Lys Ala Thr His Asn Phe Gly Asp Gly Phe Tyr Ala Gln
                 50                  55                  60

Gly Tyr Leu Glu Thr Arg Phe Val Ser Lys Tyr Lys Asp Asn Ala
                 65                  70                  75

Asp His Phe Asp Ser Ile Thr Thr Lys Tyr Ala Tyr Val Thr Leu
                 80                  85                  90

Gly Asn Lys Ala Leu Gly Glu Val Lys Leu Gly Arg Ala Lys Thr
                 95                 100                 105

Ile Ala Asp Gly Ile Thr Ser Ala Glu Asp Lys Glu Tyr Gly Val
                110                 115                 120

Leu Asn Asn Ser Lys Tyr Ile Pro Thr Asn Gly Asn Thr Val Gly
                125                 130                 135

Tyr Thr Phe Glu Gly Ile Asp Gly Leu Val Leu Gly Ala Asn Tyr
                140                 145                 150

Leu Leu Ala Gln Gln Arg Asn Ala His Ser Gly Ala Ala Gly Glu
                155                 160                 165

Val Val Ala Gln Ala Ile Ser Asn Gly Val Gln Val Gly Ala Lys
                170                 175                 180

Tyr Asp Ala Asn Asn Ile Ile Ala Gly Ile Ala Tyr Gly Arg Thr
                185                 190                 195

Asn Tyr Arg Glu Asp Leu Ala Ile Gln Asp Lys Ser Gly Lys Lys
                200                 205                 210

Gln Gln Val Asn Gly Ala Leu Ser Thr Leu Gly Tyr Arg Phe Ser
                215                 220                 225

Asp Leu Gly Leu Leu Val Ser Leu Asp Ser Gly Tyr Ala Lys Thr
                230                 235                 240

Lys Asn Tyr Lys Asp Lys His Glu Lys Arg Tyr Phe Val Ser Pro
                245                 250                 255

Gly Phe Gln Tyr Glu Leu Met Glu Asp Thr Asn Val Tyr Gly Asn
                260                 265                 270

Phe Lys Tyr Glu Arg Asn Ser Val Asp Gln Gly Lys Lys Ala Arg
                275                 280                 285
```

-continued

```
Glu His Ala Val Leu Phe Gly Val Asp His Lys Leu His Lys Gln
            290                 295                 300

Val Leu Thr Tyr Ile Glu Gly Ala Tyr Ala Arg Thr Arg Thr Asn
            305                 310                 315

Asp Lys Gly Lys Thr Glu Lys Thr Glu Lys Glu Lys Ser Val Gly
            320                 325                 330

Val Gly Leu Arg Val Tyr Phe
            335     337
```

VACCINE FOR NONTYPEABLE *HAEMOPHILUS INFLUENZAE* INFECTION

This application claims priority to U.S. provisional application No. 60/558,639, filed on Apr. 1, 2004, the disclosure of which is incorporated herein by reference.

This invention was supported by grant number AI 19641 from the National Institutes of Health. The Government has certain rights in the invention.

FIELD OF THE INVENTION

The present invention relates generally to the field of vaccines effective for *haemophilus influenzae* infections.

DISCUSSION OF RELATED ART

Bacterial infections continue to account for a considerable amount of human illness for both adults and children. Bacterial infections are often treated with antibiotics. However, the development of antibiotic resistant strains of many human pathogens has provided an impetus for developing other approaches to bacterial infections such as the use of vaccines.

A vaccine to prevent nontypeable *Haemophilus influenzae* (NTHI) infection is desired by the medical community because it would have the potential to prevent a host of infections, most notably millions of cases of childhood otitis media that cost billions of dollars to the U.S. healthcare budget. Further, NTHI is known to cause exacerbations of chronic obstructive pulmonary disease (COPD). COPD is a chronic lung disease that afflicts approximately 20 million people in the US and is the fourth most common cause of death in the US. The course of COPD is characterized by intermittent exacerbations which result in hospital admissions, respiratory failure and death in some patients. Approximately half of exacerbations are caused by bacterial infection and *H. influenzae* is the most common bacterial cause. Therefore, an effective vaccine for NTHI would have an enormous impact on the course of COPD by reducing the morbidity and mortality of these infections. However, the current problem or obstacle to designing an effective NTHI vaccine is the unusually large amount of genetic variability among designated outer membrane protein 2 (OMP P2). Immune responses to OMP P2 are usually specific to the strain from which it is derived. For this reason, OMP P2 was discarded by the scientific community and the focus shifted to other antigens which are more conserved. Thus, there remains a need compositions for use in eliciting an immune response against a broad range of NTHI strains.

SUMMARY OF THE INVENTION

In the present invention is provided a method for identification of strains of nontypeable *Haemophilus influenzae* (NTHI) for designing immunogenic compositions which can cross react with a broad range of NTHI strains. The method comprises the steps of obtaining the amino acid sequences of OMP P2 proteins from a plurality of NTHI strains; aligning and comparing the aligned sequences; generating a relatedness tree based on the sequence comparison; grouping the strains based on the relatedness of their OMP P2 sequences; and selecting representative strains from the groups for preparation of immunogenic compositions.

In another embodiment, the present invention provides immunogenic compositions comprising whole bacteria cells from the representative strains of the various groups, or OMP P2 proteins derived from the representative strains. Because these representative strains exhibit cross reactivity against other strains within their family (or group), these compositions can be used as vaccines to elicit antibodies with broad specificity to the OMP P2 proteins of a range of NTHI strains. In particular embodiments are provided compositions suitable for eliciting an immune response against at least 70% of a diverse population of NTHI strains.

BRIEF DESCRIPTION OF THE FIGURES

FIG. 2 provides the amino acid sequences of P2 proteins from strains 13P24H1 (SEQ ID NO:1), 23P2H1 (SEQ ID NO:2), 54P24H1 (SEQ ID NO:3) 47P12H1 (SEQ ID NO:4) and 31P7H1 (SEQ ID NO:5).

FIG. 5 is an expanded tabular representation of results from testing of NTHI strains for use as immunogenic compositions.

DETAILED DESCRIPTION OF THE INVENTION

In the present invention is provided a method for designing immunogenic compositions effective against a broad range of NTHI bacterial strains. The method involves identification of representative NTHI strains which can be used for preparation of vaccines effective against a broad range of NTHI strains. Whole bacteria from the identified strains or isolated OMP P2 proteins from the identified strains can be used to prepare the immunogenic compositions.

Figure 1:
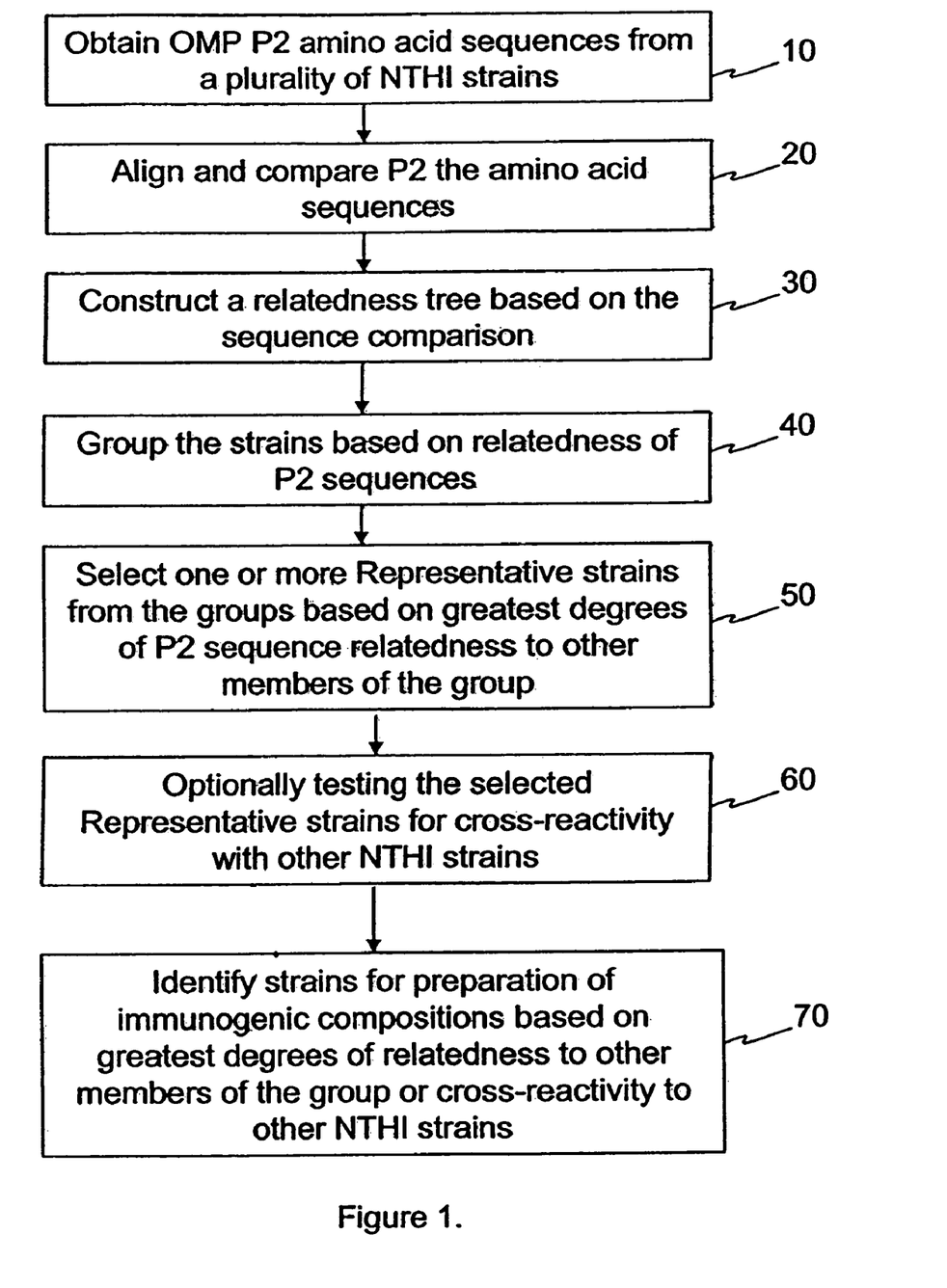
FIG. 1 is a flowchart representing the steps of the invention.

More specifically, the method comprises generating a relatedness tree based on the amino acid sequence of OMP P2 proteins and then identifying strains most representative of the entire spectrum of the strains. Referring to FIG. 1, the method comprises the steps of: (10) obtaining the amino acid sequences of OMP P2 proteins from a plurality of strains of NTHI, (20) aligning and comparing the sequences using appropriate software (such as ClustalW), (30) generating a relatedness tree (dendogram) using appropriate software (such as MACVECTOR®), (40) grouping the strains based on the relatedness of their P2 protein sequences, (50) from the groups of step (40), selecting representative strains which exhibit the greatest degrees of P2 sequence relatedness to other strains in the group, (60) optionally testing the selected representative strains to determine the degree of cross-reactivity with other NTHI strains, and (70) identifying strains for preparation of immunogenic compositions. The identified strains typically have a high degree of relatedness to other members of the group or a high degree of cross-reactivity to other NTHI strains. The representative strains or P2 proteins from the strain representatives may be used in broad-spectrum vaccines.

Amino acid sequences of OMP P2 proteins from a plurality of NTHI strains can be obtained in a number of ways known to those skilled in the art. For example, nucleotide sequences encoding outer membrane protein P2 (OMP P2) from NTHI strains can be determined and the amino acid sequences of the OMP P2 proteins deduced according to the genetic code. Purification of genomic DNA from cultures of clinical isolates of NTHI strains can be performed using standard molecular biology techniques. Portions of the NTHI genomic DNA encoding OMP P2 proteins can be obtained from the genomic DNA using restriction digests or amplification techniques such as the polymerase chain reaction (PCR) or ligase chain reaction (LCR) using synthetic oligonucleotide primers complementary to the OMP P2 protein coding regions and/or regions flanking the coding regions. The obtained portions may be purified and sequenced directly or may be subcloned into an appropriate vector, such as PUC or PGEM plasmids, transformed into bacteria, and further amplified for sequence determination. Determining the nucleotide sequences of the OMP P2 coding regions can be performed by well known methods, such as by manual or automated dideoxy sequencing reactions. Alternatively, the amino acid sequences of such proteins may be obtained from publicly available databases such as GenBank. In another alternative, the amino acid sequences of the NTHI OMP P2s may be obtained by sequencing of OMP P2 proteins purified from the NTHI strains of interest or by sequencing recombinant OMP P2 proteins derived from the strains using standard techniques.

The plurality of OMP P2 sequences can be compared by alignment techniques and relative degrees of homology calculated to obtain a relatedness tree, also referred to herein as a dendogram.

Generating a relatedness tree begins with sequence alignments. Alignment of sequences can be conducted, e.g., by computerized implementations of homology algorithms, such as ClustalW, GAP BESTFIT or PILEUP. Homology algorithms create a multiple sequence alignment from a group of related sequences using progressive, pairwise alignments. The alignment procedure begins with the pairwise alignment of the two most similar sequences, producing a cluster of two aligned sequences. This cluster can then be aligned to the next most related sequence or cluster of aligned sequences, after which the process is repeated. The final alignment is achieved by completion of a series of progressive, pairwise alignments.

A relatedness tree can be generated from sequence alignments using computer programs. One example of a computer program suitable for generating relatedness trees is MACVECTOR®, available from ACCELRYS®.

Once obtained, the relatedness tree may be used to group the strains according to the degree of homology between the OMP P2 amino acid sequences. In general, dendograms can be understood to be formed of branching arms. The lengths of the arms of the dendogram reflect the degree of similarity among the sequences, where shorter arms separating two sequences indicate that the sequences are similar, while longer arms indicate that the sequences are more divergent. Numerical values may be assigned to the arms by computer programs such that the similarity of the aligned sequences is quantified. By inspection of the dendogram, related strains can be grouped according to the length of their connecting arms or from the numerical values assigned thereto. From the identified groups, a particular strain or strains representative of the group can be selected for use with representatives of other groups in broad-spectrum vaccines. It is preferable that the P2-amino acids sequences of representative strains have high degrees of relatedness with the other members of their group. High degrees of relatedness as used herein means more than 85% identity in amino acid sequences between the strain representative and other members of the group. For preparation of the immunogenic compositions of the invention, it is preferable to use a representative strain or strains with the highest degree of P2 sequence relatedness to the other strains in its group.

The group representatives can be tested for the ability to elicit a broad immune response against NTHI strains in a variety of ways known to those skilled in the art. For example, a complement-dependent bactericidal assay can be performed by inoculating mammals, such as mice, with whole bacteria of the NTHI strains or OMP P2 proteins purified from the strains. Serum subsequently collected from the inoculated mice is added to suspensions of the NTHI bacterial strains to be tested. Active complement is then added to the test samples and the suspension is spread onto culture plates. Relative killing strength is calculated as the percent reduction in colony forming units in the test sample relative to that in a control sample in which heat inactivated complement is used in place of active complement. Without intending to be bound by any particular theory, it is considered that a positive killing result is due to the formation of antibodies in the mice that cross-react with the strain killed. Further, a greater number of strains of NTHI killed is considered indicative of a broader specificity of the strain used as the inoculant. By inspection of the breadth and strength of NTHI killing by the serum of the inoculated animals, NTHI strains used as the inoculants can be selected for use as in immunogenic compositions, such as broad-specificity vaccines.

In additional embodiments, the group representatives can be tested for the ability to elicit a broad immune response against NTHI strains using immunoassay techniques such as ELISA assays or fluorescent activated cell sorting (FACS).

The compositions can undergo optional further rounds of testing for the ability to elicit immune responses against additional NTHI strains. The dendogram branches can then be reconfigured to account for additional detected specificities, if any.

In another embodiment, the present invention provides immunogenic compositions comprising whole cell bacteria from more than one NTHI strain, or OMP P2 protein derived therefrom, effective in eliciting an immune response against a plurality of NTHI strains, whether or not the strains are identified by the method of the present invention.

Accordingly, in one embodiment, the present invention provides immunogenic compositions comprising whole cell bacteria from more than one NTHI strain. In preferred embodiments, the immunogenic compositions comprise bacteria from five or more NTHI strains, wherein each strain can elicit an immune response to at least one NTHI strain other than itself. Eliciting an immune response against a strain distinct from the immunizing strain is also referred to herein as "cross-reacting." It is preferable that each strain can elicit an immune response to two or more strains, or even more preferably, three or more strains other than itself. In particular embodiments, the strains used in the immunogenic compositions may be any of strains 13P24H1, 23P2H1, 54P24H1, 47P12H1, 31P7H1, 32P8H2 or 6P5H.

In another embodiment, the immunogenic compositions comprising whole cell bacteria can elicit an immune response to at least ten NTHI strains not included in the immunogenic compositions. In general, it is preferred the immunogenic compositions can elicit an immune response to at least 70% of the strains present in a diverse population of cells. It is more preferable that the immunogenic composition can cross react with at least 80% or at least 90% of the strains present in a diverse population of cells. As used herein, "a diverse population of cells" means samples of NTHI clinical isolates obtained from a plurality of individuals. The individuals may be from different geographic regions. A convenient number of samples in a diverse population of cells is one-hundred NTHI clinical samples. It will be recognized by those skilled in the art that while the absolute number of clinical isolates (i.e., the number of individual samples) in a diverse population is not important, a large enough sample is desired so that a statistically meaningful estimate of a test composition's cross reactivity can be obtained. The clinical samples may be obtained and/or cultured from the nasopharynx, middle ear fluid or sputum of an individual using standard microbiological techniques.

The NTHI strains may be used in whole cell vaccines. In this regard, a "whole cell vaccines" includes vaccines comprising live, attenuated or killed whole bacteria. For preparation of the latter, the bacteria may be killed by techniques well known to those in the art, such as heat killing, formaldehyde or formalin killing.

For example, to produce a killed whole cell vaccine of the invention, viable NTHI cells can be cultured and exposed to formalin for a sufficient period of time to kill 100% of the cells. Typically, formalin concentrations range from about 1% to about 5% (v/v). Suitable exposure times for a particular formalin concentration to achieve 100% killing may be readily determined from standard killing curves. Following culture in media, the cells may be concentrated, for example, by centrifugation, and the cell pellet and culture fluid separated. The killed cells may be prepared for administration by formulation in a pharmaceutically acceptable carrier such as water, physiological saline, mineral oil, vegetable oils, aqueous sodium carboxymethyl cellulose, or aqueous polyvinylpyrrolidone.

In another embodiment is provided immunogenic compositions comprising OMP P2 proteins from at least two NTHI strains for eliciting an immune response against a plurality of NTHI strains. In a preferred embodiment, the present invention provides immunogenic compositions comprising purified or recombinant OMP P2 proteins from at least five NTHI strains. By "derived from" it is meant that the P2 proteins are purified from the NTHI strains or have an amino acid sequence identical to P2 proteins purified from the strains. In particular embodiments, the P2 proteins have the amino acid sequences of SEQ ID NO:1 through SEQ ID NO:5 derived from strains 13P24H1 (GenBank accession no. AY051383), 23P2H1 (GenBank accession no. AY051393), 54P24H1 (GenBank accession no. AY051401), 47P12H1 (GenBank accession no. AY051397), 31P7H1 (GenBank accession no AY051396), respectively, or amino acid sequences derived from strains $^{32}$P8H2 or 6P5H. The amino acid sequences of SEQ ID NO:1 through SEQ ID NO:5 are provided in FIG. 2.

It is preferable that each of the P2 proteins can elicit an immune response against at least one P2 protein other than itself. In a preferred embodiment, each P2 protein can elicit an immune response to at least three P2 proteins other than itself.

In another embodiment, the immunogenic compositions comprising P2 proteins can elicit an immune response to at least ten P2 proteins not included in the immunogenic compositions. In yet another embodiment, the immunogenic compositions comprising P2 proteins can elicit an immune response to the P2 proteins from at least 70% of the strains from a diverse population of cells.

P2 proteins may be obtained by methods known to those skilled in the art, such as by purification from NTHI strains directly, or produced as recombinant proteins from expression vectors inserted into cells.

For example, outer membrane components of NTHI cells can be prepared from a total cell membrane fraction. Total membrane fractions are typically prepared by differential sedimentation after disruption of the cells by methods such as sonication, grinding, or expulsion from a french press or other homogenization device. The total membrane fraction may then be fractionated into inner and outer membranes by density gradient sedimentation or by differential solubilization of the inner membrane constituents with detergents. Solubilization of the P2 protein from the outer membrane-fraction can then be achieved using techniques known to those skilled in the art. After solubilization, further purification of the protein can be achieved by standard methods including but not limited to ion exchange, hydrophobic and reverse phase chromatography, affinity chromatography and preparative electrophoresis.

In another embodiment, the OMP P2 proteins can be obtained by cloning DNA sequences encoding the proteins into a suitable expression vector, transforming a suitable host with the expression vector to obtain an expression system and purifying recombinant proteins from the expression system. DNA sequences encoding the P2 proteins can be readily obtained as described above for determining the nucleotide sequences encoding the P2 proteins. The P2 encoding DNA may be inserted into expression vectors and introduced into a host cell by methods described in many standard laboratory manuals, such Sambrook, et al., MOLECULAR. CLONING: A LABORATORY MANUAL, 2nd Ed., Cold Spring Harbor Laboratory Press, Cold Spring Harbor, N.Y. (1989). Without being limited, examples of suitable techniques for inserting the expression vectors into a host cell include calcium phosphate transfection, DEAE-dextran mediated transfection, transvection, microinjection, cationic lipid-mediated transfection, electroporation and transduction. Representative examples of appropriate hosts include but are not limited to bacterial cells, such *E. coli*, and fungal cells, such as the yeast *Saccharomyces*.

Generally, any system or vector suitable to maintain, propagate or express polynucleotides and/or to express the P2 proteins may be used for expression in this regard. A variety of expression systems can be used to produce the P2 proteins from the strains of NTHI identified by the invention. Such vectors include but are not limited to vectors derived from bacterial plasmids and bacteriophage, from yeast chromosomal elements, and from viruses and vectors derived from combinations thereof, such as cosmids and phagemids.

Recombinant P2 proteins of the present invention can be recovered and purified from cell cultures by well-known methods including ammonium sulfate or ethanol precipitation, acid extraction, anion or cation exchange chromatography, phosphocellulose chromatography, hydrophobic interaction chromatography, affinity chromatography or ion metal affinity chromatography. Further, well known techniques for refolding proteins may be employed to regenerate the native conformation of the proteins if they become denatured during intracellular synthesis, isolation and/or purification.

Vaccines comprising whole cells or proteins can be prepared by methods known to those skilled in the art. In one embodiment, broad spectrum vaccines comprising NTHI P2 proteins can be prepared by mixing the purified or recombinant proteins with pharmaceutically acceptable carriers. Also, such vaccines may also contain adjuvants or other pharmaceutically active agents as are conventional in the art, including mucosal adjuvants, such as type II heat-labile enterotoxins, and chitosans. Further, the P2proteins may be delivered in liposomal compositions.

The vaccines of the present invention may be administered to an individual by any acceptable method of delivery which enables the composition to elicit an immune response to a plurality of NTHI strains. Examples not meant to be limiting include subcutaneous, intramuscular, intravenous, intradermal, intranasal, oral or by inhalation.

The compositions of the invention may be administered in a single dose or in more than one dose. In one embodiment, the composition is administered as a single dose adequate to induce a sufficient immune response to prophylactically or therapeutically treat an NTHI infection in an individual. In alternate embodiments, the composition is administered as several doses over a period of time, as a primary vaccination and "booster" vaccinations.

The following Examples are meant to illustrate particular embodiments of the invention and are not meant to be limiting.

EXAMPLE 1

Figure 3:
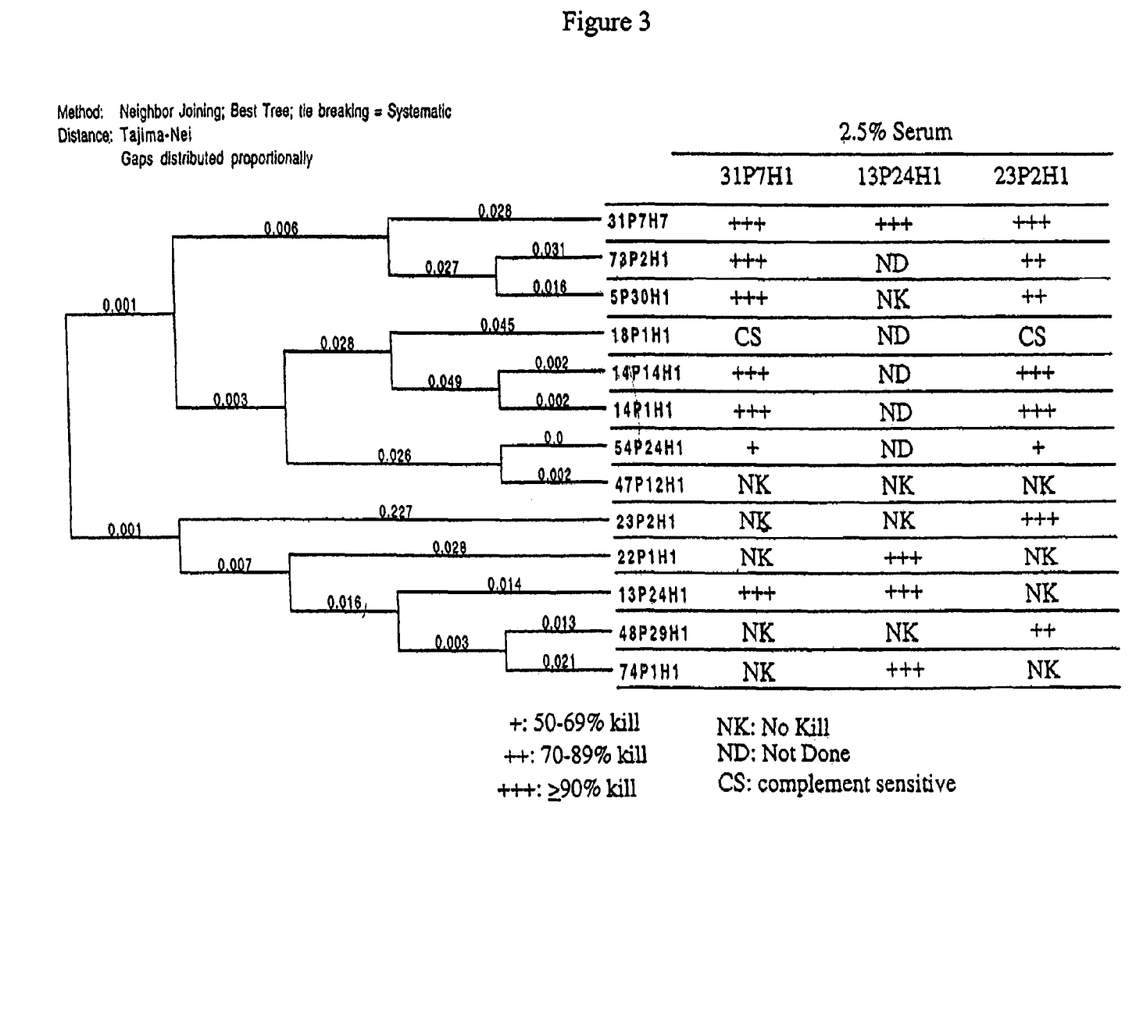
FIG. 3 is a dendogram obtained using the method of the invention, and further depicts results from selection and testing of NTHI strains for use as immunogenic compositions.

This Example demonstrates grouping and selecting representative strains of NTHI for use in immunogenic compositions of the invention. Accordingly, FIG. 3 depicts a dendogram of OMP P2 proteins derived from 13 strains of NTHI obtained from a study clinic. The position of each strain and the value provided above the lines of the branches are indicators of genetic relatedness. Thus, the OMP P2 of strain 23P2H1, with a branch number of 0.227 units, is distantly related to the other sequences in the tree, and therefore it can be assumed that 23P2H1 comprises its own family. In contrast, strain 13P24H1 occupies a central location among several surrounding strains and may therefore be deemed a representative of this family. The upper three strains in the dendogram (31P7H7, 73P2H1, and 5P30H1) are considered related to each other and strain 31P7H7 was chosen as this family's representative. A fourth family comprised of 18PH1, 14P14H1, 14P1H1, 54P24H1, and 47P12H1, is found in the center of the dendogram. Strain 54P24H1 was chosen as this family's representative. However, 54P24H1 was not used in the first round of immunizations in an attempt to limit the number of strains used in the vaccine.

EXAMPLE 2

This Example demonstrates the use of immunogenic compositions comprising, group representatives to elicit antibody responses against the NTHI strains in the immunogenic compositions, as well as antibodies against a plurality of NTHI strains not included in the immunogenic compositions.

Groups of mice were immunized with either strain 31P7H7, 13P24H1, or 23P2H1. Whole bacteria were used to immunize the mice because it is known that immunization of mice with whole NTHI results in an antibody response almost exclusively to the OMP P2 expressed by the strain.

The sera was collected from the mice and used in a bactericidal reaction in which serum is mixed with the live bacteria and complement, and the killing of the bacteria in one hour is determined. To the right of the dendogram of FIG. 3 are presented results of bactericidal assays in which each of the mouse sera, at a concentration of 2.5%, were tested against each of the strains in the dendogram. These results demonstrate that serum from mice immunized with strain 31P7H1 tended to kill most of the strains nearest to it on the dendogram. Likewise, serum from mice immunized with strain 13P24H1 tended to kill the strains in its family. These results were expected if the mice were responding to the OMP P2 of the immunizing strain. Surprisingly, serum from strain 23P2H1 had broad activity and killed several strains through the dendogram. There was also overlap in which one strain was killed by several sera. FIG. 3 also demonstrates that 11 of the 12 testable strains were killed by serum from mice immunized with either 13P24H1 or 23P2H1. An exception in the bactericidal data was the failure to kill strain 47P12H1 which is a member of the family represented by strain 54P24H1. However, in a subsequent experiment, strain 47P12H1 was killed by serum from mice immunized with strain 54P24H1. By inspection of the data from FIG. 3, vaccines comprising whole cells of strains 13P24H1, 23P2H1 or 54P24H1 were formulated.

To confirm the role of antibodies to OMP P2 in the bactericidal assays, experiments were performed to evaluate the extent to which bactericidal antibodies in serum raised to whole bacteria were directed at the P2 protein. Antiserum to strain 13P24H1 was generated in Balb/c mice by intraperitoneal injection of whole organisms in phosphate buffered saline. The serum exhibited bactericidal activity of 50% or greater against the homologous strain at serum concentrations of 0.02% and higher. To investigate the presence of bactericidal antibodies to P2, aliquots of the antiserum were adsorbed against strain 13P24H1, as well as a P2 deficient mutant of 13P24H1. If bactericidal antibodies are directed at P2, then antiserum adsorbed with the P2 mutant should retain bactericidal activity while antiserum adsorbed with the parent strain will show a loss of bactericidal activity. Unadsorbed serum was included as a positive control.

The results summarized in Table 1 demonstrate that adsorption with the parent strain showed a loss of bactericidal activity at all dilutions, while the same serum adsorbed with the P2 mutant retained bactericidal activity at serum concentrations of 0.625% and higher.

TABLE 1

| % serum | Unadsorbed | Adsorbed with wild type strain 13P24H1 | Adsorbed with P2 mutant of 13P24H1 |
| --- | --- | --- | --- |
| 5 | 81.1 | 0 | 35.5 |
| 2.5 | 94.6 | 0 | 66.3 |
| 1.25 | 88.7 | 0 | 29.9 |
| 0.625 | 99.7 | 0 | 39.7 |
| 0.313 | 95.9 | 0 | 0 |
| 0.16 | 99.5 | 0 | 0 |

In Table 1, presented are results of bactericidal assays with aliquots of antiserum to whole organisms of strain 13P24H1. Numbers indicate the percentage of cells killed in the bactericidal assays. Results are representative of 2 independent experiments. The results in Table 1 indicate that a significant proportion of the bactericidal antibodies in the antiserum raised to whole bacteria of strain 13P24H1 are directed towards outer membrane protein P2.

Thus, this Example demonstrates that immunization with NTHI whole bacteria elicits an immunological response against to P2 proteins, and to a plurality of NTHI strains not included in the immunogenic compositions.

EXAMPLE 3

Figure 4:
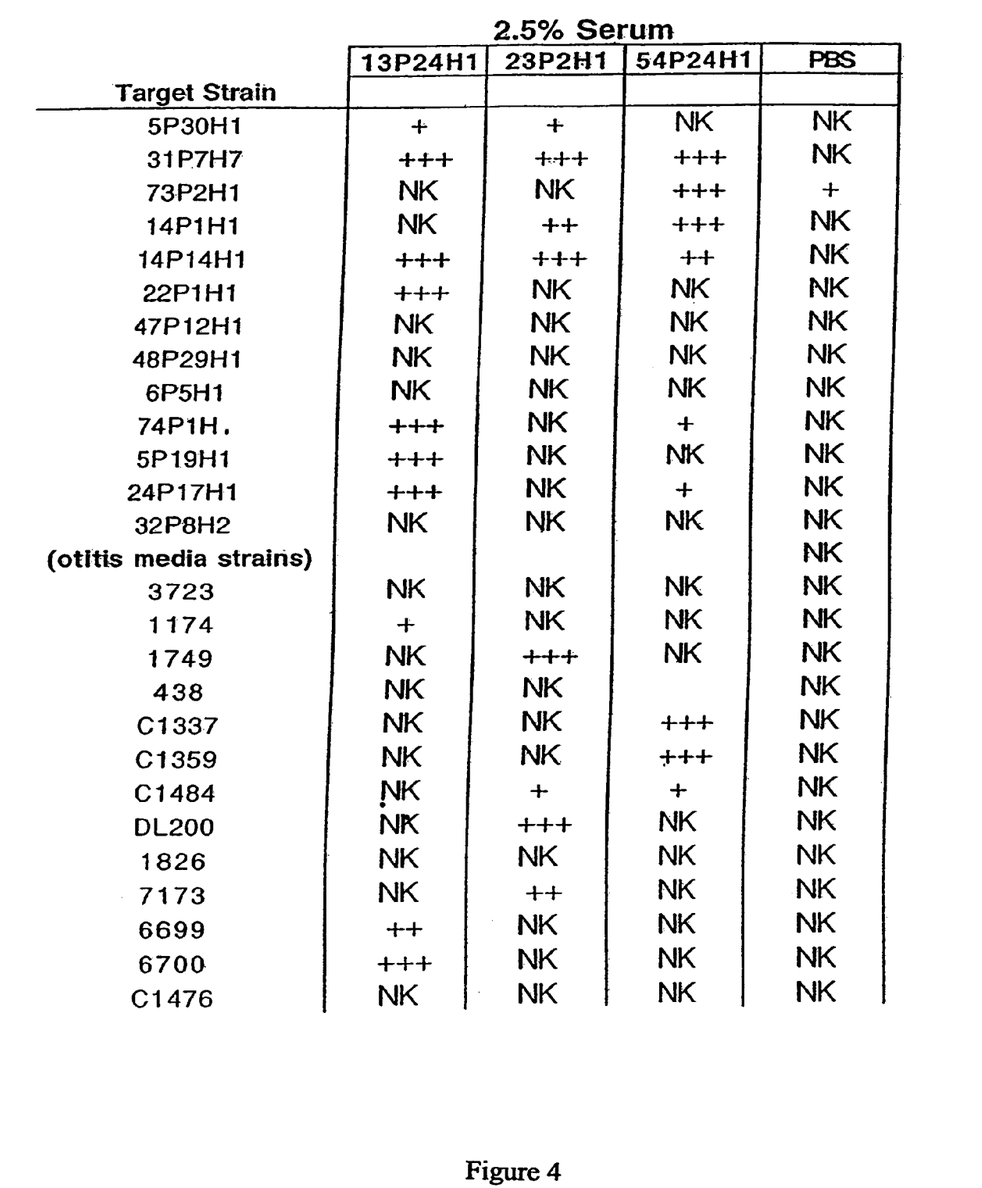
FIG. 4 is a tabular representation of results from testing NTHI strains for use as immunogenic compositions.

This Example demonstrates the use of immunogenic compositions to elicit an immune response against a panel of NTHI strains. The strains used for immunization are listed across the top of the figure. Some of the target strains are repeated from the dendogram of FIG. 1, while others were collected either from the COPD study clinic or were obtained from children with otitis media. While strains 47P12H1 and 48P29H1 were not killed in the second round of immunizations/bactericidal assays (FIG. 4), these strains were killed in the first set of experiments (FIG. 3), indicating this effect may be due to differences in immune responses by the mice. Overall, 69% (9/13) of the NTHI strains and 69% (18/26) were killed by at least one of the sera. Note also that serum from mice immunized with phosphate-buffered saline (PBS) alone had no activity (with the exception for strain 72P2H 1, which was minimal).

EXAMPLE 4

This Example demonstrates additional immunogenic compositions that can elicit an immune response against a plurality of NTHI strains.

Strains 13P24H1, 23P2H1, 54P24H1, 47P12H1, 32P8H2, 65PH1 and 31P7H7 were identified as group representatives using the method of the invention. As depicted in FIG. 5, each of the strains has broad NTHI killing specificity. Thus, this Example demonstrates the preparation of immunogenic compositions that can elicit an immune response against a range of NTHI strains obtained from a variety of geographical regions.

---

The invention claimed is:

1. An immunogenic composition comprising at least five nontypeable *Haemophilus influenzae* (NTHI) outer membrane protein P2 (OMP P2) proteins, wherein each of the OMP P2 proteins is derived from a different NTHI strain, wherein each of the OMP P2 proteins can elicit an immune response against at least one NTHI strain from which the OMP P2 protein in the composition was not derived.

2. The immunogenic composition of claim 1, wherein each of the OMP P2 proteins can elicit an immune response against at least two NTHI strains from which the OMP P2 proteins in the composition were not derived.

3. The immunogenic composition of claim 1, wherein each of the OMP P2 proteins can elicit an immune response against at least three NTHI strains from which the OMP P2 proteins in the composition were not derived.

4. The immunogenic composition of claim 1, wherein each of the OMP P2 proteins can elicit an immune response against at least ten NTHI strains from which the OMP P2 proteins in the composition were not derived.

5. The immunogenic composition of claim 1, wherein the composition can elicit an immune response against at least 70% of clinical isolates of NTHI obtained from a plurality individuals.

6. The immunogenic composition of claim 1, wherein said at least five OMP P2 proteins have the amino acid sequence of SEQ ID NO: 1, SEQ ID NO: 2, SEQ ID NO: 3, SEQ ID NO: 4 and SEQ ID NO: 5 respectively.

7. The immunogenic composition of claim 1, further comprising an adjuvant.

8. The immunogenic composition of claim 1, further comprising liposomes.

9. The immunogenic composition of claim 1, wherein the immunogenic composition is present in a pharmaceutical preparation suitable for administration to an individual through a route selected from subcutaneous, intramuscular, intravenous, intradermal, intranasal and oral administration.

* * * * *